United States Patent [19]
Harjunmaa et al.

[11] Patent Number: 5,895,838
[45] Date of Patent: Apr. 20, 1999

[54] METHOD FOR CORRECTING A LIQUID DISPENSING ERROR, AND A LIQUID DISPENSING DEVICE

[75] Inventors: Hannu Harjunmaa, Holden, Mass.; Osmo Suovaniemi, Helsinki, Finland

[73] Assignee: Biohit Oy, Helsinski, Finland

[21] Appl. No.: 08/983,116

[22] PCT Filed: Jul. 5, 1996

[86] PCT No.: PCT/FI96/00398

§ 371 Date: Jan. 7, 1998

§ 102(e) Date: Jan. 7, 1998

[87] PCT Pub. No.: WO97/02893

PCT Pub. Date: Jan. 30, 1997

[30] Foreign Application Priority Data

Jul. 7, 1995 [FI] Finland .................... 953344
Mar. 22, 1996 [FI] Finland .................... 961337

[51] Int. Cl.$^6$ ........................... B01L 3/02
[52] U.S. Cl. .............................. 73/864.13
[58] Field of Search ............ 73/863.01, 863.02, 73/864.11, 864.13, 864.16; 422/100; 141/130, 318; 374/142

[56] References Cited

U.S. PATENT DOCUMENTS

4,976,161 12/1990 Czernecki et al. .............. 73/864.17
5,187,990 2/1993 Magnussen, Jr. et al.
5,287,758 2/1994 Geiss et al.

FOREIGN PATENT DOCUMENTS

0337460 A2 10/1989 European Pat. Off.

OTHER PUBLICATIONS

Rodgerson et al., Clin. Chem. 20/1, 43–50, 1974; Sources of Error in Spectrophotometric Measurement of Aspartate Aminotransferase and Alanine Aminotransferase Activities in Serum; accepted Oct. 29, 1973.

Pardue et al, Clin. Chem 20/8, 1028–1042, 1974;Photometric Errors in Equilibrium and Kinetic Analyses Based on Absorption Spectroscopy; accepted Apr. 28, 1974.

Hattori; Super Pipetter Seminar; pp. 1–64 (as cited on p. 2 of the present specification no date available).

Osmo Suovaniemi; Automated Instrumentation for Clinical and Research Labratories, Innovations and Development of Vertical Light Beam Photometers and Electronic Pipettes; Feb. 4,1994; pp. 1–51 and appendices.

*Primary Examiner*—Robert Raevis
*Attorney, Agent, or Firm*—Birch, Stewart, Kolasch & Birch, LLP

[57] ABSTRACT

The object of the invention is a method for correcting a temperature dependent dispensing error occurring during liquid dispensing, such as pipetting, as well as a liquid dispensing device, such as a pipette, having a higher degree of accuracy. According to the method the dispensing takes place by means of two chambers connected to each other over a gas passage. The first chamber communicates, in addition to the gas passage, with the liquid to be dispensed, and the second chamber is gas tight except for the gas passage. In order to receive liquid in the dispensing device, the volume of the second chamber is increased, resulting in gas flowing therein from the first chamber, and in turn, liquid to be dispensed flowing into the first chamber until a pressure equilibrium between the chambers has been reached. According to the invention the change in temperature of the gas flowing from the first chamber to the second is measured, and the change in volume effected in the second chamber is corrected based on the measured temperature change so that the desired quantity of liquid is received in the first chamber. For the temperature measurement, a temperature sensor mounted in the second chamber in the vicinity of the gas passage and in addition, possibly also a sensor mounted in the first chamber is used.

11 Claims, 2 Drawing Sheets

5,895,838

METHOD FOR CORRECTING A LIQUID DISPENSING ERROR, AND A LIQUID DISPENSING DEVICE

This application is the national phase under 35 U.S.C. §371 of prior PCT International Application No. PCT/FI 96/00398 which has an International filing date of Jul. 5, 1996 which designated the United States of America, the entire contents of which are hereby incorporated by reference.

BACKGROUND OF THE INVENTION

The object of the present invention is a method for eliminating a temperature dependant dispensing error in connection with the dispensing of liquids.

Specifically the invention is used in connection with a dispensing method, wherein the dispensing takes place by means of two chambers connected to each other over a gas passage, wherein the first chamber communicates, in addition to the said gas passage, with the liquid to be dispensed, and the second chamber is gas tight except for the said gas passage, whereby, in order to take up liquid in the dispensing device, the volume of the second chamber is increased, resulting in gas flowing therein from the first chamber, and in turn, liquid to be dispensed flowing into the first chamber until a pressure equilibrium between the chambers has been reached.

The object of the invention is also a liquid dispensing device comprising two chambers interconnected over a gas passage, the first chamber communicating, in addition to the said gas passage, with the liquid to be dispensed, and the second chamber being gas tight except for the said gas passage, and containing means for regulating the volume thereof.

The method according to the invention is applied typically, but not solely, when pipetting liquids using an electronic or mechanical pipette, and it allows for the elimination of or at least a substantial reduction of a liquid dispensing error resulting from temperature differences between the sample and the pipette.

In laboratory analyses pipetting and dispensing of samples and reagents which are usually in liquid form comprises the most difficult stage in the process of obtaining an accuracy of, for example, less than half a percent in accuracy as well as in reproducibility. The pipetting accuracy using the more old-fashioned technique has usually been in the magnitude of one microliter (with an inaccuracy of even 5 to 10%, especially at smaller volumes), if not worse (Rodgerson et al, Clin. Chem. 20/1, 43–50, 1974 and Pardue et al, Clin. Chem. 20/8, 1028–1042, 1974). Using the modern techniques of today, the accuracy of both mechanical and electronic pipettes varies in the range of 0.1–5% (Suovaniemi: Dissertation, ISBN 952-90-5248-0, University of Helsinki, 1994).

The pipetting inaccuracy depends on both the apparatus and also its user. The effect of human error is more often evident especially in connection with the use of mechanical pipettes as compared to the use of electronic pipettes. The quality of the pipette tip and the manner of its use has its own small effect, except when the tip is placed on to the pipette by hand. In this case the tip may become contaminated or compressed so that the tip regains its shape during the first pipetting operations and in connection therewith draws an excess liquid into the tip. This error can be eliminated e.g. by using vertically packaged tips or by handling the tips with extreme care without changing their form when mounting them on a pipette. The use of an electronic pipette removes the human pipetting errors, as well as the use of automatic calibration of an electronic pipette in connection with each use (Hattori, Super Pipetter Seminar: Standardized Risk Factor and Support to Validation, Biohit, 1994). Improving these factors usually leads to pipetting results which are only 0.1–0.5% more accurate.

SUMMARY OF THE INVENTION

According to the invention a method is now provided for eliminating or at least reducing substantially temperature dependent dispensing errors occurring in liquid dispensing methods based on the air-displacement principle.

The object of the invention is achieved by a method and device according to the appended claims.

Specifically, the method according to the invention is characterized in that the change in temperature of the gas flowing from the first chamber to the second is measured, and the change or increase in volume caused in the second chamber for taking up liquid, is corrected based on the said measured temperature change so that the desired quantity of liquid is received in the first chamber.

According to the invention the said temperature change is measured prior to liquid sampling with temperature sensors suitably located in each chamber, whereby one measures the temperature of the gas in the first chamber, and the second measures the temperature prevailing in the second chamber, that is the temperature which the gas flowing from one chamber to the other during liquid sampling reaches. The difference in these temperatures corresponds to the temperature change of the gas flowing from the first chamber to the second.

According to a second embodiment of the invention the method can be carried out using only one sensor, which is placed in the second chamber. This sensor measures first the temperature of the second chamber prior to liquid sampling, and a second time, during liquid sampling, the temperature of the gas flowing from the first chamber to the second chamber, the difference being the said change in temperature.

An object of the invention is also a liquid dispensing device of the afore mentioned type which is characterized in that a temperature sensor is provided for measuring the change in the temperature of the gas flowing from one chamber to the other via the gas passage, and means for feeding a corresponding correction command to the volume regulating means in the second chamber.

According to the invention, both chambers can contain a sensor, or alternatively only the second chamber contains a sensor.

In the following, the invention is described as applied to liquid dispensing by pipetting and an electrical pipette, but the invention is not limited to pipettes, but it can be applied in a variety of liquid dispensing systems within the scope of the appended claims.

The invention is based on the observation that the quantity of air which in the drawing stage of pipetting flows from the pipette tip to the pipette body quickly attains the temperature of the pipette body. The change in the volume of the air space in the body which is caused by moving the plunger of the pipette in order to draw liquid into the pipette tip, is equal to the selected pipetting volume, i.e. the pipette set value. As a result of the plunger movement, the pressure in the body decreases, and air flows from the tip into the body until the pressures are substantially in balance again. In case the temperatures of the air space in the tip and the pipette body are not equal, the final volume of the quantity of air moved is, after evening out of the temperatures, different in the pipette body from the volume that was intended to be removed from the tip. The difference between the nominal and real volumes of the quantity of air transferred, is also the volumetric error of the liquid received in the tip.

The evening out of the temperature in the pipette body takes place rapidly as the air passage there is relatively narrow, i.e. the distance of all the air molecules from the closest wall is small, usually less than 1 mm. In addition the specific heat capacity of air is small compared to the specific heat capacity of the material of the body. The air entering the body attains the temperature of the body before the tip has been lifted out of the sample, wherefore the changed volume of the air transferred affects directly the pipetting result. In the beginning and the end of pipetting the pressures inside and outside the pipette are substantially in equilibrium, and any transient pressure differences do not affect the end result.

An important consequence of this observation is that there is no need to measure the temperature of the liquid. Decisive is the temperature of the air space from which air moves to the pipette body, and specifically the temperature difference between that air space and the body. After a few pipettings, the air space within the tip reaches substantially the temperature of the liquid, but measuring the temperature of the air space in the tip makes a correction possible which is correct from the beginning on. It is also to be observed that the correction according to this invention also eliminates any error resulting from a deviating tip temperature. Such a situation is present, for example, when applying a tip with warm fingers.

In the following a correction formula is derived which has to be used by the processor in connection with an electrical pipette, for it to be able to change the movement of the plunger from its set value so that the quantity of liquid to be drawn is of the desired magnitude in all temperature conditions.

The formula for calculation is derived from Gay-Lussac's law which stipulates that at constant pressure the volume of a gas is proportional to its absolute temperature. It is assumed that the absolute temperature of the pipette body is $T_p$ and the absolute temperature of the air space of the tip is $T_k$ (see also FIG. 1). The nominal pipetting volume, i.e. the set value, is V. In the initial stage the tip is immersed in the liquid, but not so deeply that the hydrostatic pressure is capable of substantially forcing liquid into the tip. Now the plunger is drawn back to a degree corresponding to the volume V and the pressure inside the pipette body decreases. As there is a tendency to re-establish the pressure equilibrium, air at a temperature of $T_k$ in a volumetric amount V flows from the tip into the pipette body. This quantity of air is now subjected to the temperature $T_p$. In other words, the new volume V' of the air transferred is according to the Gay-Lussac's law $$V'=(T_p/T_k)V.$$

As pressure equilibrium has to be established at the end, a further volume of air $$\Delta V=V-V'=(1-T_p/T_k)V.$$

has to transfer between the tip and the body. As this air comes from the tip, due to the pressure equilibrium, it has to be replaced by an equal volume of liquid, and the pipetting error is $\Delta V$. It is positive (too big a pipetting result) if $T_k>T_p$, and negative (too small a pipetting result) if $T_k<T_p$. In the positive results, there is an additional small excess as also $\Delta V$ is subjected to the temperature $T_p$. This is of no practical consequence, but can easily be taken into account, if desired.

The actual pipetting result V" as a function of the nominal volume (the movement of the plunger) V and the temperatures is consequently $$V''=V+\Delta V=(2-T_p/T_k)V.$$

The correction can be implemented in an electronic pipette in a straightforward manner. The temperatures can be read continuously at specific short intervals, or only when pushing the pipetting button, and according to these and the nominal volume, an activation command corresponding to $V_k$ (the corrected volume) is given to the plunger:

$$V_k=V/(2-T_p/T_k).$$

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
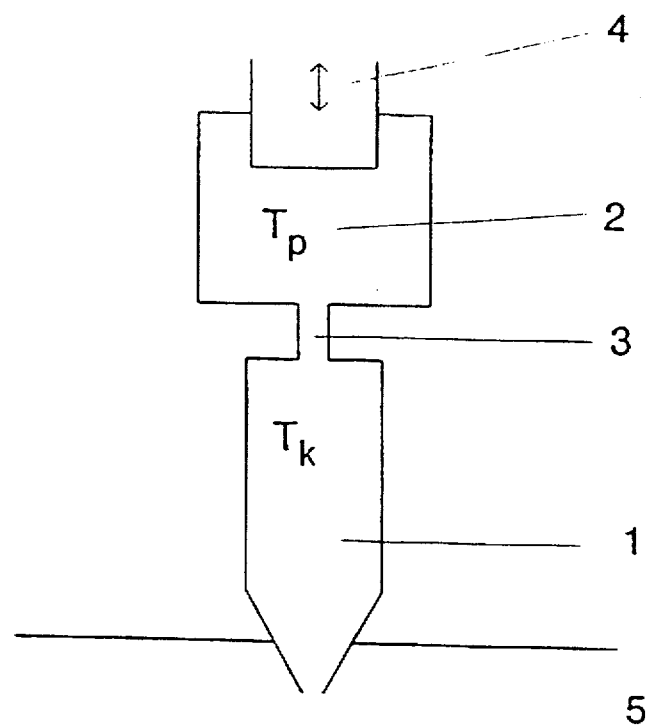
FIG. 1 shows in a general and schematic manner a liquid dispensing device according to the invention.

In FIG. 1, two gas filled chambers for receiving liquid are shown, a first chamber 1 and a second chamber 2, which communicate over a gas passage 3. The interior pressure of the chambers are substantially in balance at the beginning and the end of liquid sampling. The volume of the second chamber 2 can be enlarged in order to receive liquid by suitable means, for example by means of a reciprocating plunger 4 mounted in a gas-tight manner in the chamber 2. The first chamber 1 can be made to communicate with the liquid 5. As a result of the pressure difference brought about by the movement of the plunger 4, liquid flows into the chamber 1 until a pressure equilibrium is essentially established. The accurate liquid volume received in the chamber 1 is thereafter dispensed in one or more further dishes. In the system, a quantity of gas thus moves from one chamber to the other. The quantity corresponds to the liquid volume to be drawn, the volume of which, however, during drawing of the liquid or thereafter, changes in case the temperature of the chambers is not uniform. If this change in gas volume cannot be taken into account, a dispensing error results.

Figure 2:
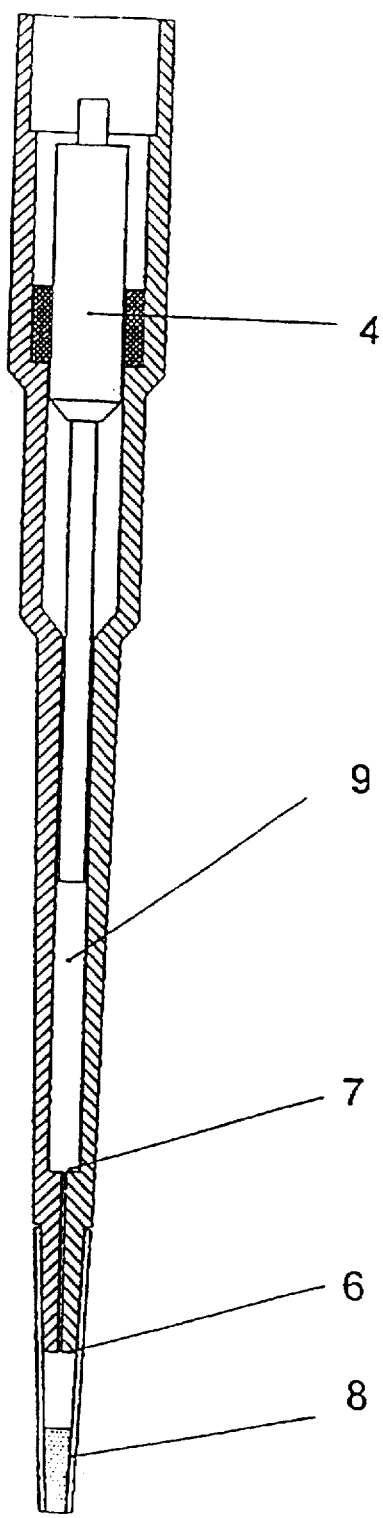
FIG. 2 shows in a schematic manner a pipette according to the invention for carrying out the method.

FIG. 2 shows a pipette, which comprises a cylinder space forming the air space 9 of the pipette, the cylinder space having a gas connection to the pipette tip 8, a reciprocating plunger 4 in the cylinder space, and operating means for the plunger (not fully shown). According to a preferred embodiment of the invention, the pipette comprises sensors 6 and 7 for measuring the temperature. A suitable means for measuring the temperature is, for example, an NTC resistance (Negative Temperature Coefficient resistance) functioning as a temperature sensor. Such resistances are known per se and commercially available. According to this embodiment, the temperature of the gas is measured by the sensors 6 and 7 in the tip 8 and the air space 9 before liquid sampling, and the temperature difference measured is used for feeding a correction command to the operating means for moving the plunger in accordance with the formula derived earlier.

Figure 3:
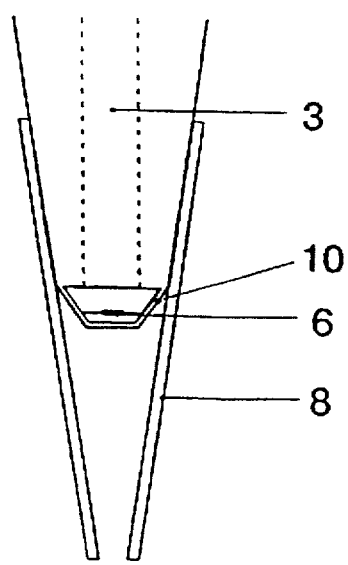
FIG. 3 shows a constructional and mounting system for a sensor for measuring the temperature.

In FIG. 3 a favorable embodiment for attaching a sensor to the dispensing device, for example a pipette body, is shown. In FIG. 3, there is disclosed on an enlarged scale an interchangeable tip 8, into which the lower part of the pipette body projects with its gas passage 3 extending into the air space 9 of the pipette. The sensor 6 is fastened to a handle-like device 10 opening towards the body, and attached between the legs of the handle, the sensor 6 extending into the air space of the tip itself. The handle-like device 10 functions, besides as a fastening means, also as a means for protecting the sensor. It is self-evident that also the sensor 7 in the air space can be constructed in a manner corresponding to the embodiment shown. The device 10 has to be dimensioned so that neither it, nor the sensor 6, is brought into contact with the liquid to be dispensed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for correcting a temperature dependant dispensing error occurring during dispensing of a liquid, wherein the dispensing takes place by means of two chambers connected to each other over a gas passage, wherein the first chamber communicates, in addition to the gas passage, with the liquid to be dispensed, and the second chamber is gas tight except for the gas passage, whereby, in order to take up liquid in the dispensing device, the volume of the second chamber is increased, resulting in gas flowing therein from the first chamber, and in turn, liquid to be dispensed flowing into the first chamber until a pressure equilibrium between the chambers has been reached, comprising the steps of:

measuring the change in temperature of the gas flowing from the first chamber to the second; and correcting the volume in the second chamber for taking up liquid based on the measured temperature change so that a desired quantity of liquid is received in the first chamber.

2. The method according to claim 1, further comprising the step of measuring the interior temperature of both chambers prior to liquid sampling by means of sensors mounted separately in each chamber.

3. The method according to claim 1, further comprising the steps of: measuring the change in the gas temperature with a sensor placed in the second chamber prior to liquid sampling by measuring the interior temperature of the chamber and during liquid sampling by measuring the temperature of the gas flowing from the first chamber to the second.

4. A liquid dispensing device comprising: two chambers interconnected over a gas passage, the first chamber communicating with the gas passage, and with liquid to be dispensed, and the second chamber being gas tight except for communicating with the gas passage, and containing means for regulating the volume thereof, wherein a temperature sensor is provided for measuring a change in the temperature of the gas transferring from the first chamber to the second chamber; and means are provided for feeding a corresponding correction command to the volume regulating means in the second chamber.

5. The liquid dispensing device according to claim 4, wherein both chambers contain a temperature sensor.

6. The liquid dispensing device according to claim 4, wherein only the second chamber contains a temperature sensor.

7. The liquid dispensing device according to claim 4, wherein the temperature sensor is an NTC-sensor.

8. The liquid dispensing device according to claim 4, wherein the means for regulating the volume in the second chamber is a plunger mounted gas-tightly in the chamber.

9. The liquid dispensing device according to claim 4, wherein the first chamber is a pipette tip.

10. The liquid dispensing device according to claim 7, wherein the first chamber is comprised of a preferably detachable pipette tip, and the second chamber is comprised of an air space formed in a pipette body, communicating with the pipette tip by means of the gas passage through the body, wherein the sensor is over a mounting device fastened to the body, in the close vicinity of the gas passage between the tip and the air space.

11. The liquid dispensing device according to claim 10, wherein the mounting device is a handle and the sensor is mounted between the legs of the handle, the ends of the legs being attached to the body of the device.

* * * * *